(12) United States Patent
Stoop

(10) Patent No.: US 6,370,220 B1
(45) Date of Patent: Apr. 9, 2002

(54) METHOD OF AND DEVICE FOR FLUORESCENT X-RAY ANALYSIS OF A SAMPLE

(75) Inventor: Marinus Gerardus Maria Stoop, Almelo (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/691,809

(22) Filed: Oct. 19, 2000

(30) Foreign Application Priority Data

Oct. 21, 1999 (EP) .............................. 99203450

(51) Int. Cl.⁷ .............................................. G01N 22/00
(52) U.S. Cl. .............................. 378/45; 378/49; 378/50
(58) Field of Search .............................. 378/50, 44, 45, 378/46, 49

(56) References Cited

U.S. PATENT DOCUMENTS

| 5,062,127 A | * 10/1991 | Sayma et al. | 378/45 |
| 5,396,529 A | * 3/1995 | Grodzins | 378/45 |
| 6,173,037 B1 | * 1/2001 | Brouwer | 378/45 |

FOREIGN PATENT DOCUMENTS

JP 2706601 1/1988

* cited by examiner

Primary Examiner—Robert H. Kim
Assistant Examiner—Hoon Koo Song

(57) ABSTRACT

The invention relates to a method for fluorescent X-ray analysis of a sample, which sample includes: a substrate (5) containing a chemical element b; a thin layer (6) which is deposited on the substrate and contains the chemical element b and a chemical element a, which method includes the steps of: irradiating the sample by means of primary X-rays, detecting the intensity of X-ray lines of comparatively hard fluorescent X-rays and comparatively soft fluorescent X-rays, both produced in the sample due to irradiation by means of the primary X-rays, wherein one or more of the following combinations of the fluorescent X-ray lines of the chemical elements a and b are detected:

b-L/b-K;
b-K/a-L;
b-L/a-L;
b-L/a-M;
a-M/a-L
a-M/a-N
a-K/b-K
a-K/b-L
a-K/a-L;

and the thickness of the thin layer (6) and/or the concentration of the first or the second chemical element are detected on the basis of the detected X-ray lines of the comparatively hard and the comparatively soft fluorescent X-rays.

6 Claims, 2 Drawing Sheets

METHOD OF AND DEVICE FOR FLUORESCENT X-RAY ANALYSIS OF A SAMPLE

FIELD OF THE INVENTION

The invention relates to a method for analysis of a sample which includes:
a substrate containing a chemical element b,
a thin layer which is deposited on the substrate and contains the same chemical element b and a chemical element a, the method including the steps of:
irradiating the sample by means of primary X-rays,
detecting the intensity of X-ray lines of comparatively hard fluorescent X-rays and of comparatively soft fluorescent X-rays, both generated in the sample due to the irradiation by means of the primary X-rays.

DESCRIPTION OF PRIOR ART

The invention also relates to a device for carrying out the above method.

A method and a device of this kind are known from Japanese patent No. 2706601. The cited Japanese patent describes a method for determining the thickness of a thin layer on a substrate and for determining the concentration of a chemical element in said thin layer by means of fluorescent X-ray analysis. To this end, the sample is irradiated by means of X-rays (the primary radiation) originating from an X-ray source. The sample is formed by a substrate which consists of a first chemical element, in this case being silicon, on which there is provided a thin layer which consists of the first chemical element (silicon) and a second chemical element, in this case being tungsten. The primary radiation generates fluorescent X-rays in the sample, which fluorescent X-rays contain characteristic radiation of the chemical elements present in the sample, so silicon and tungsten. This characteristic radiation includes comparatively hard X-rays (for example, having a wavelength of the order of magnitude of from 0.02 to 1 nm) as well as comparatively soft X-rays (for example, having a wavelength of the order of magnitude of from 2 to 15 nm).

According to the known method the apparatus response is determined by means of the known reference samples. Using such an apparatus response, the layer thickness and the concentration of one of the chemical elements in the layer, for example tungsten, are determined on the basis of the measured intensities of both the comparatively hard and the comparatively soft fluorescent radiation. Such a determination is performed by means of a known method for the theoretical calculation of the intensity of fluorescent X-rays; this calculation method is known as the "fundamental parameter method". Such a theoretically calculated intensity of fluorescent X-rays is the intensity occurring immediately after departure from the sample; therefore, the effect of the entire measuring channel from the sample up to and including the detector is not taken into account therein. In the cited Japanese patent the combination of the two types of fluorescent X-rays (i.e. the comparatively hard and the comparatively soft fluorescent rays) is formed by one of the combinations of X-ray lines K with M, K with N and L with N of tungsten or one of the combinations of X-ray lines K with M, K with N and L with N of silicon.

The known method, however, has the drawback that only a limited number of combinations of X-ray lines is used for the analysis of the sample, so that the possibility for analysis are severely restricted. For example, a thin layer of cobalt silicide is not covered by said method.

SUMMARY OF THE INVENTION

It is an object of the present invention to provide a method and a device wherein said drawback is mitigated.

To this end, according to the invention one or more of the following combinations of X-ray lines of the chemical elements a and b are detected:
b-L/b-K;
b-K/a-L;
b-L/a-L;
b-L/a-M;
a-M/a-L;
a-M/a-N;
a-K/b-K;
a-K/b-L;
a-K/a-L;
and the thickness of the thin layer and/or the concentration of the first or the second chemical element is determined on the basis of the X-ray lines determined for the comparatively hard and for the comparatively soft fluorescent X-rays.

In conformity with a further aspect of the invention there is provided a device for carrying out the above-mentioned method, including:
a sample holder for receiving the sample to be analyzed;
an X-ray source for producing the primary X-rays;
selection means for the selection at option of at least the comparatively hard and the comparatively soft X-rays;
detection means for detecting the intensity of the X-ray lines of the fluorescent X-rays emitted by the sample;
wherein the selection means include a first selector which is arranged in a first channel so as to select the comparatively soft fluorescent X-rays and a second selector which is arranged in a second channel so as to select the comparatively hard fluorescent X-rays; and
the detection means include a first detector which is arranged in a first channel and a second detector which is arranged in a second channel, said detectors simultaneously detecting the comparatively hard and the comparatively soft fluorescent X-rays.

Because of the simultaneous detection of the comparatively hard and the comparatively soft fluorescent X-rays in separate channels, the period of time required for detection can be reduced. Moreover, the selection means, detection means and focusing means, if any, can be selected so as to optimize the detection sensitivity in each channel.

In a further preferred embodiment, the pressure in each of the channels is less than $10^{-6}$ bar, thus enabling the analysis of comparatively light elements.

BRIEF DESCRIPTION OF THE DRAWING

Further advantages, features and details of the present invention will be elucidated hereinafter in the description of preferred embodiments. In the description reference is made to the following Figures.

DETAILED DESCRIPTION OF THE PREFERRED EMBODIMENTS

Figure 1:
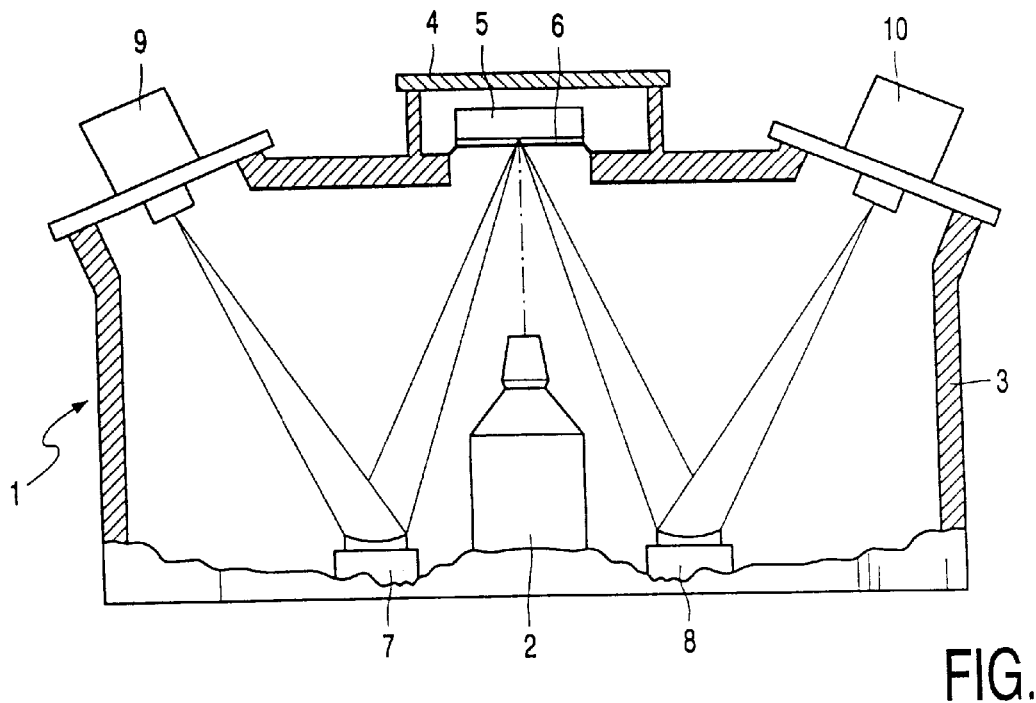
FIG. 1 is a diagrammatic view of a fluorescent X-ray spectrometer according to the invention.

FIG. 1 shows diagrammatically a fluorescent X-ray spectrometer 1. An X-ray tube 2, accommodated in a housing 3, emits primary X-rays in the direction of a sample 5, 6 which is mounted in a holder 4. The sample includes a substrate 5 which is made, for example, of silicon and on which there is provided a thin layer 6 which is made of, for example cobalt. Due to the irradiation of the material of the sample by the primary X-rays, photoelectrons are emitted by the atoms of the sample. This creates electron holes in one or more of the shells of the relevant atom, thus making the atom unstable. In order to restore the stability of the atom, the holes in the inner shell are filled by electrons from the outer shell. Such transitions are accompanied by an energy emission in the form of secondary X-rays or fluorescent radiation. The various electron shells are referred to as K, L, M, N etc., each shell corresponding to a given energy level. Consequently, the energy level of the fluorescent radiation is determined by the difference in energy at the transition between the various shells of the atom. Because the energy level of the emitted fluorescent radiation is proportional to the frequency of the radiation, frequency analysis can be performed on the fluorescent X-rays so as to determine which transitions occur. This information is used to determine the type of atom and hence the chemical composition of the irradiated sample. Measuring also the intensity of the fluorescent radiation yields a measure of the concentration of each of the various elements in the sample.

The fluorescent radiation is detected by intercepting the radiation by means of analysis crystals 7 and 8, each of which reflects radiation of a predetermined wavelength only. The reflected radiation is collected by respective detectors 9 and 10. Thus, the wavelength of the radiation collected by the detectors 9 and 10 is adjusted by appropriate positioning of the analysis crystals 7 and 8.

The detectors 9 and 10 are provided with electronic means for converting the detected fluorescent X-rays into an output signal which is representative of the intensity of the detected fluorescent X-rays.

One of the analysis crystals, for example the analysis crystal 7, is constructed so as to select comparatively hard fluorescent radiation (for example, radiation having a wavelength of the order of magnitude of from 0.02 to 2 nm). The other analysis crystal, in this case being, for example the analysis crystal 8, is constructed, for example, so as to select comparatively soft fluorescent radiation (for example, radiation having a wavelength of the order of magnitude of from 2 to 15 nm).

Figure 2:
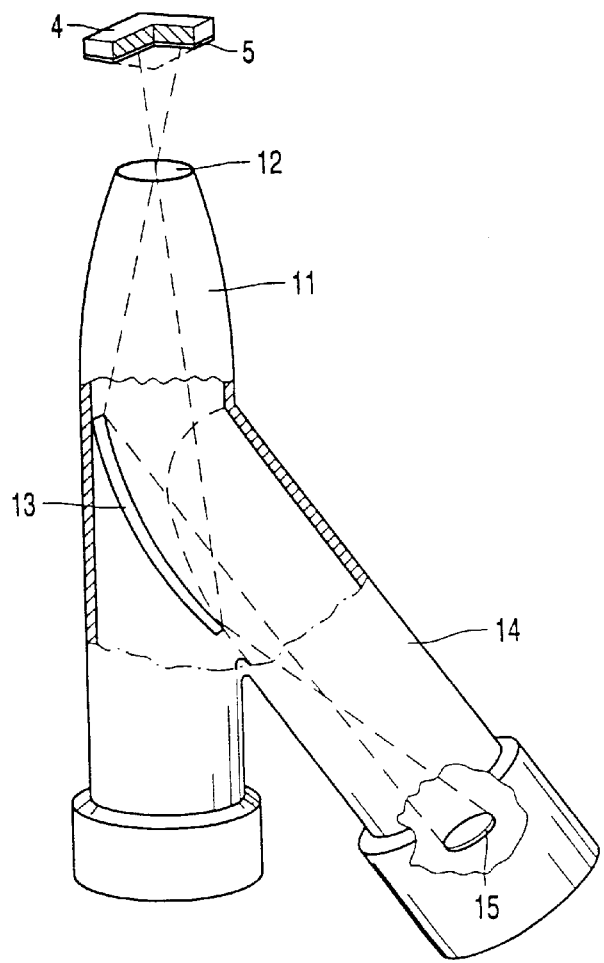
FIG. 2 is a partly exploded perspective view of a preferred embodiment of a channel according to the invention.

FIG. 2 shows a preferred embodiment of a channel for the detection of fluorescent X-rays. Fluorescent radiation emanating from the sample 4, 5 enters, via a diaphragm 12, an elongated tube 11 and is deflected by an analysis crystal 13, arranged in the tube 11, so as to travel in the direction of a tube 14 which is contiguous with the tube 11 and in which there is arranged a detector 15. Such an embodiment of a channel enables a better signal-to-noise ratio to be achieved with a lower detection limit.

A comparatively low pressure of $10^{-6}$ bar can be achieved in such a channel 11, 14, thus offering an enhanced signal-to-noise ratio of the fluorescent X-rays detected by the detector 15 in comparison with known channels. Moreover, the length of the channel is comparatively small in relation to the lengths used according to the state of the art. Consequently, the fluorescent X-rays need travel only a limited distance in the channel, so that the signal-to-noise ratio is improved further.

The determination of the concentration of the chemical element in the thin layer and the thickness of the thin layer on the basis of the measured intensities of the comparatively hard and the comparatively soft fluorescent X-rays will be described in detail hereinafter.

When a known sample (that is, a sample of known composition and dimensions) is exposed to X-rays from a known X-ray source (that is, a source whose spectral composition is fully known), the intensity of a given wavelength of the fluorescent radiation can be calculated. The algorithm for this calculation is generally known as the "fundamental parameter method". The intensity thus calculated will be referred to herein as the calculated theoretical intensity or $I_{calc,th}$. Thus, the latter quantity will have different values for the various wavelengths. A number of samples of known, mutually different composition can be taken (the reference samples) and the theoretical intensity $I_{calc,th}$ thereof can be determined at different wavelengths. These samples can also be subjected to measurements in accordance with the invention, the intensity thus being measured at said wavelengths. This intensity will be referred to hereinafter as the measured intensity or $I_m$. The calculated theoretical intensity $I_{calc,th}$ and the measured intensity $I_m$ are thus determined for each sample and for each of said wavelengths. For each of said wavelengths of the fluorescent radiation, therefore, a (for example, graphic) relationship can be established between $I_{calc,th}$ and $I_m$. This relationship will be called the calibration curve hereinafter.

Figure 3:
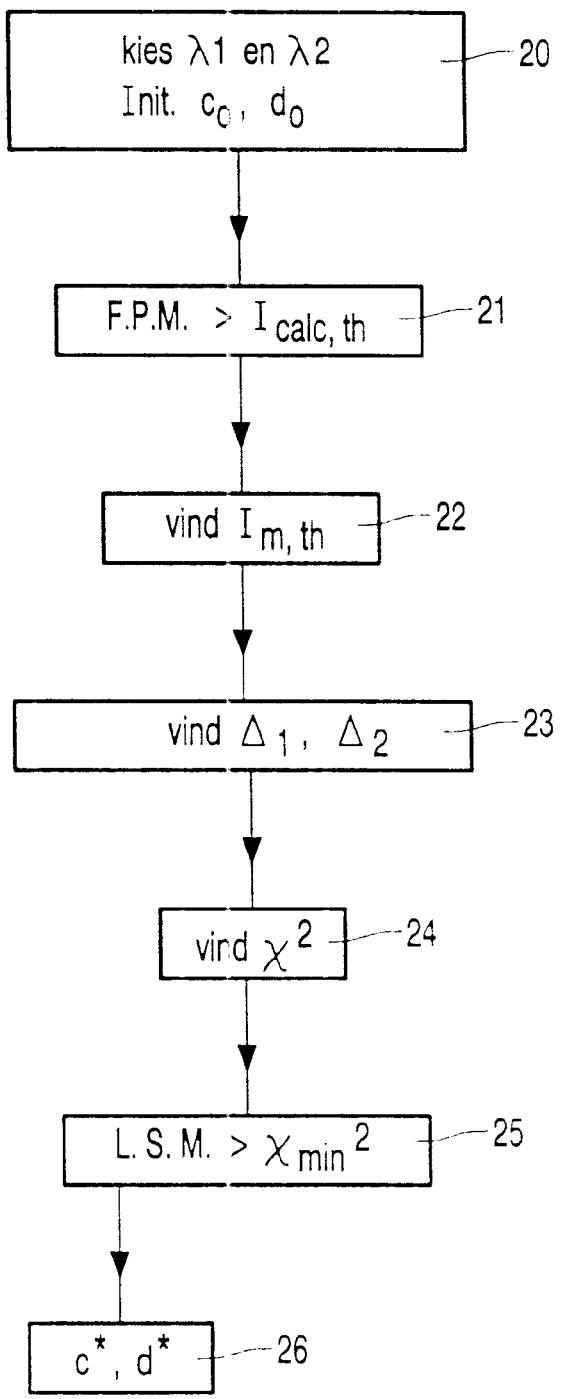
FIG. 3 shows a flow chart illustrating the determination of the thickness of the thin layer and/or the concentration of the chemical elements of the sample.

FIG. 3 shows a flow chart illustrating the calculations in conformity with the invention. The calculations are started by determining the wavelengths $\lambda_1$, $\lambda_2$ of the measured X-ray lines. Moreover, an assumption is made as regards arbitrary starting values $c_0$ and $d_0$ for the concentration to be calculated for the relevant chemical element in the thin layer and for the thickness of the thin layer (20) to be calculated. The theoretical intensity $I_{calc,th}$ is determined for each of the two wavelengths by means of the fundamental parameter method (FPM) (21).

Subsequently, the calibration curves which are associated with the spectrometer configuration and represent the relationship between theoretically calculated fluorescent intensities and associated measured fluorescent intensities are used to read the associated calculated measured intensity $I_{m,th}$ (22) from the calculated theoretical intensity $I_{calc,th}$. Subsequently, the difference between the calculated measured intensity and the actually measured intensities is determined, i.e. the differences $\Delta_1 = I_{m,th} - I_m$ and $\Delta_2 = I_{m,th} - I_{m2}$ are determined (23). $\Delta_1$ and $\Delta_2$ are a measure of the deviation of the arbitrary starting values $c_0$ and $d_0$ of the concentration to be calculated and the thickness of the thin layer from the actual concentration c and the actual thickness d; the known chi-square ($\chi^2$) test in conformity with $\chi^2 = \Delta_1^2 + \Delta_2^2$ (24) can be applied to derive a measure of the total deviation.

Subsequently, the values of $c_0$ and $d_0$ are adapted each time in conformity with a known iteration method, for example, the least squares minimization algorithm (least squares method or LSM) until the deviation is minimum according to a statistical measure (25). The values of the concentration and the thickness at which such a statistical measure is minimum constitute the searched concentration c* and thickness d* (26). It is to be noted that the above optimization process can be performed in a large number of ways which are known from statistics.

What is claimed is:
1. A method for analysis of a sample (5, 6) which includes:
   a substrate (5) containing a chemical element b;
   a thin layer (6) which is deposited on the substrate and contains the same chemical element b and a chemical element a, the method including the steps of:

irradiating the sample by means of primary X-rays, detecting the intensity of X-ray lines of comparatively hard fluorescent X-rays and of comparatively soft fluorescent X-rays, both generated in the sample (5, 6) due to the irradiation by means of the primary X-rays, wherein one or more of the following combinations of X-ray lines of the chemical elements a and b are detected:

b-L/b-K;
b-K/a-L;
b-L/a-L;
b-L/a-M;
a-M/a-L;
a-M/a-N;
a-K/b-K;
a-K/b-L;
a-K/a-L;

and the thickness of the thin layer (6) and/or the concentration of the first or the second chemical element is determined on the basis of the X-ray lines determined for the comparatively hard and for the comparatively soft fluorescent X-rays.

2. A method as claimed in claim 1, wherein the chemical element b contains silicon.

3. A method as claimed in claim 1, wherein the chemical element a contains cobalt.

4. A device for carrying out the method claimed in claim 1, including:

a sample holder (4) for receiving the sample to be analyzed;

an X-ray source (2) for producing the primary X-rays, selection means (7, 8; 13) for the selection at option of at least the comparatively hard and the comparatively soft X-rays, detection means (9, 10; 15) for detecting the intensity of the X-ray lines of the fluorescent X-rays emitted by the sample (5, 6), wherein the selection means (7, 8; 13) include a first selector (7) which is arranged in a first channel so as to select the comparatively soft fluorescent X-rays and a second selector (8) which is arranged in a second channel so as to select the comparatively hard fluorescent X-rays, and the detection means include a first detector (9) which is arranged in a first channel and a second detector (10) which is arranged in a second channel, said detectors simultaneously detecting the comparatively hard and the comparatively soft fluorescent X-rays.

5. A device as claimed in claim 3, wherein the pressure in each of the channels is less than $10^{-6}$ bar.

6. A device as claimed in claim 4, wherein the chemical elements contain tungsten, silicon and/or tantalum.

* * * * *